United States Patent [19]

Scarlett

[11] 4,274,407
[45] Jun. 23, 1981

[54] FLUID INJECTION SYSTEM

[75] Inventor: John A. Scarlett, Southfield, Mich.

[73] Assignee: Med Pump, Inc., Lansdowne, Pa.

[21] Appl. No.: 93,288

[22] Filed: Nov. 13, 1979

[51] Int. Cl.³ .............................................. A61J 7/00
[52] U.S. Cl. .............................. 128/213 R; 128/216;
128/214 F
[58] Field of Search ........... 128/213, 215, 216, 214 R,
128/214 F, DIG. 12, DIG. 1, 224, 230, 260

[56] References Cited

U.S. PATENT DOCUMENTS

| | | | |
|---|---|---|---|
| 3,923,060 | 12/1975 | Ellinwood, Jr. | 128/260 |
| 4,044,764 | 8/1977 | Szabo et al. | 128/214 F |
| 4,077,405 | 3/1978 | Haerten et al. | 128/214 F |
| 4,085,747 | 4/1978 | Lee | 128/218 A |
| 4,140,117 | 2/1979 | Buckles et al. | 128/213 |

Primary Examiner—John D. Yasko

Attorney, Agent, or Firm—Wood, Herron & Evans

[57] ABSTRACT

A fluid injection system including a flexible bag fluid reservoir acted upon by an elastically deformable compression member for pressurizing the fluid within the reservoir, a combined pump and valve assembly connected to the reservoir, and an injection means consisting of a flexible conduit and needle connected to the output of the combined pump and valve assembly. Also included is a selectively actuable electromagnetic force generator which cooperates with a magnetically polarized pump element and a movable magnetically polarized valve closure element, both of which are located within the combined pump and valve assembly and movable under the action of the electromagnetic force generator for accumulating and pumping a predetermined charge of fluid from the reservoir to the flexible conduit for injection into the body via the needle.

27 Claims, 8 Drawing Figures

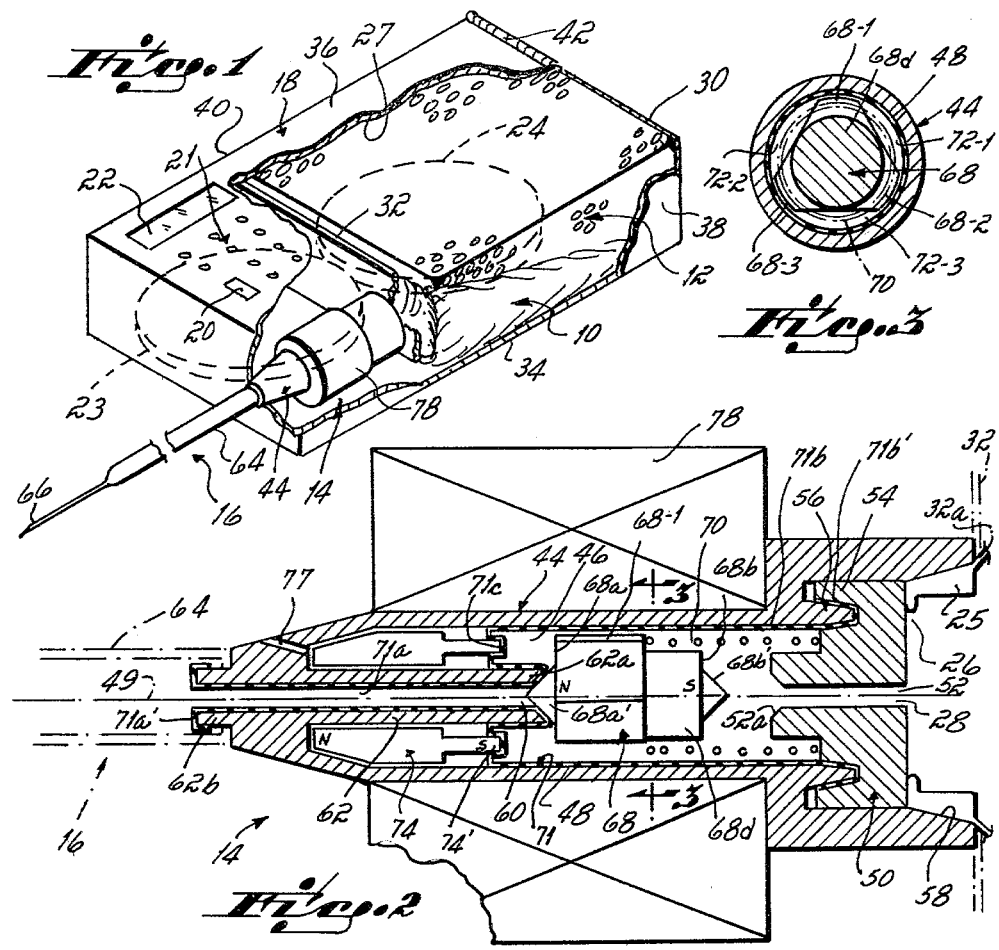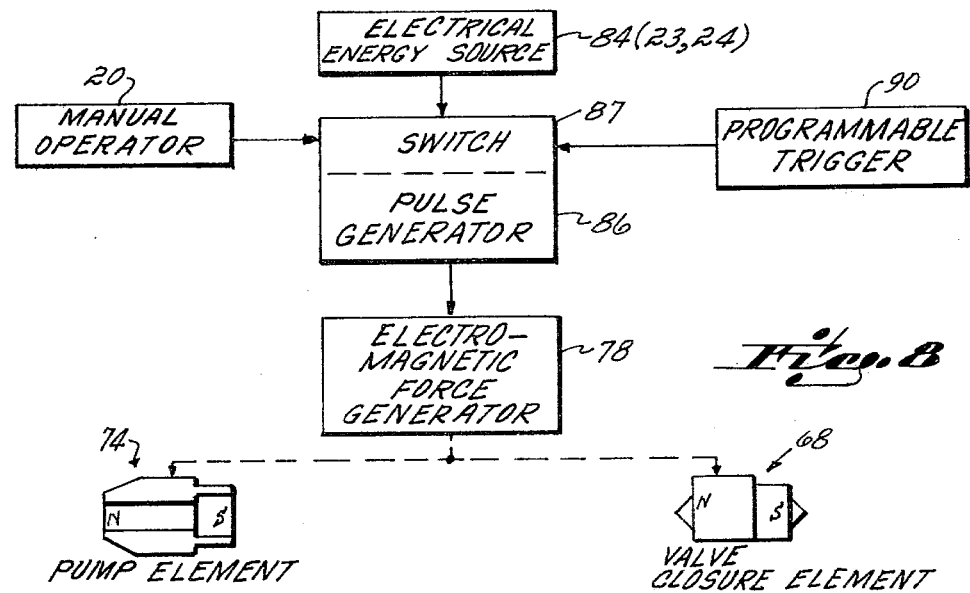

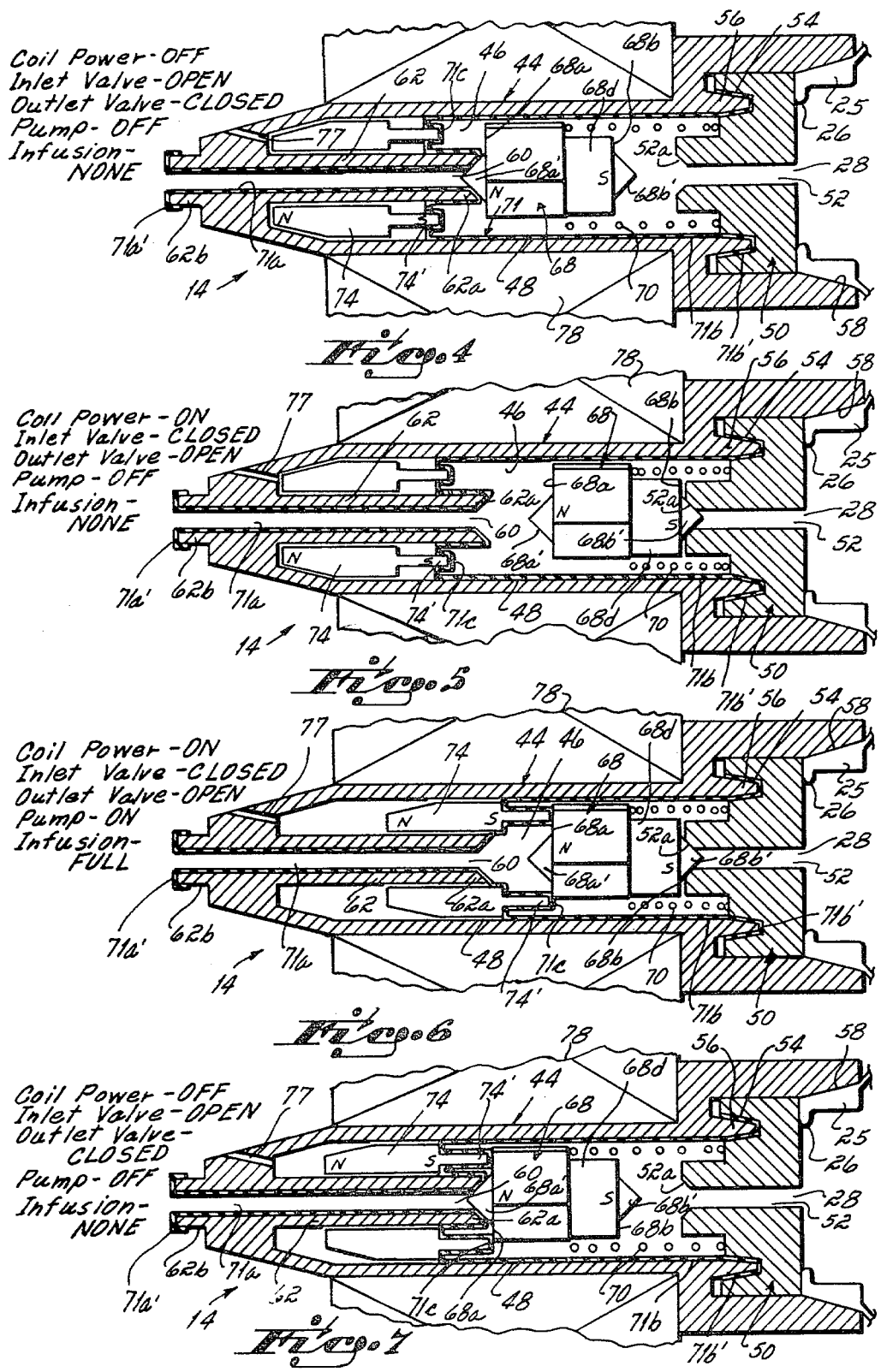

FLUID INJECTION SYSTEM

This invention relates to fluid injection systems, and more particularly to an apparatus and method for intermittently injecting a charge of fluid of predetermined quantity into the body and at a uniform flow rate.

The effective treatment of certain illnesses, such as diabetes and pneumonia, often requires predetermined medication levels to be maintained in the body. In the past, this has been most frequently achieved by injecting the patient with rather substantial doses of medication at periodic, but extended duration, intervals, such as once every 24 hours. More recently, it has been discovered that enhanced treatment results are forthcoming when the desired medication level is maintained by a series of much smaller doses injected at more frequent, shorter intervals, such as once or more often per hour. To facilitate periodic injection of medication in accordance with this latter approach, and to do so conveniently and reliably, it is necessary that the fluid injecting system, and in particular the pump, valving, fluid reservoir and associated controls, should be compact and lightweight. Only in this manner can the injecting apparatus be conveniently and unobtrusively attached directly to the body at the site of the injection.

It is also desirable, if not a commercial necessity, that the fluid reservoir, pump and valve be of such simple and inexpensive construction that they can be disposable. In this way, it is not necessary to refill the device periodically, which when required, is inconvenient, as well as difficult to accomplish when sterility is a requisite.

It is also necessary that the fluid injecting system be sufficiently rugged to withstand normal mechanical shock and abuse encountered in use.

Further, the administration of medication and management of certain illnesses requires that the medication not only be injected in accordance with a predetermined program, but also that the capability exist for supplementing the programmed injections with random doses which may vary both as to frequency and quantity. For example, in the treatment of diabetes, in addition to the programmed dosage, the injecting apparatus must be capable of injecting medication prior to each separate meal or snack, which doses vary in amount, depending upon the carbohydrate content of the contemplated meal or snack.

Additionally, and since the medication may be injected when the patient is standing, such as at work during the day, or when the patient is lying down, such as at night when the patient is asleep, the injecting apparatus must be operative regardless of position or spatial orientation of the patient.

Accordingly, it has been an objective of this invention to provide a fluid injection system which satisfies the operating requirements set forth above. This objective has been accomplished in accordance with certain of the principles of this invention by providing, in combination with a source of pressurized fluid and a conduit insertable in the body having a passage through which fluid passes for injection, a combined valve and pump assembly which includes:

(A) An internal fluid chamber provided with a fluid inlet port connected to the pressurized fluid reservoir and a fluid outlet port connected to the injection conduit;

(B) A valve closure element located within the chamber which is movable between a fluid charge accumulation position in which the closure element seals the fluid outlet port and unseals the fluid inlet port, allowing a charge of fluid of predetermined quantity to accumulate in the chamber, and an injection position in which the closure elements seal the inlet port and unseal the outlet port, permitting the accumulated charge to be pumped into the conduit for injection;

(C) A pump element located for movement within the chamber through a pumping stroke between a nonpumping position in which the volume of the chamber is at a maximum to facilitate accumulation of a fluid charge when the closure element is in its charge accumulation position, and a pumping position in which the volume of the chamber is reduced to less than the maximum to forcibly displace and transfer the accumulated fluid charge from the chamber into the conduit when the closure element is in its injection position; and (D) Actuating means for selectively alternatively placing the closure element and pump element in either (1) their charge accumulation and nonpumping positions, respectively, to facilitate transfer of a fluid charge from the pressurized reservoir to the chamber, or (2) in their injection and pumping position, respectively, to pump the accumulated fluid charge from the chamber to the conduit for injection into the body.

In a preferred form of the invention, and in accordance with further principles of this invention, the valve closure element and the pump element are permanently magnetically polarized, and a spring is provided for biasing the valve closure element toward its charge accumulation position in which the outlet port from the fluid chamber to the conduit is closed, and the inlet port from the reservoir to the fluid chamber is open. Also included is an electromagnetic force generator acting on the valve closure element and the pump element which is periodically energized to move the valve closure element and the pump element to their injection and pumping positions, respectively, and thereby effect pumped transfer of an accumulated fluid charge from the chamber to the conduit for injection into the body. After the charge has been transferred from the chamber to the conduit, the electromagnetic force generator is de-energized. The valve closure element is then returned by the spring to its charge accumulation position to admit pressurized fluid from the reservoir into the chamber, facilitating accumulation of a charge for the next injection cycle. The pressurized fluid entering the chamber is also effective to move the pump element to its nonpumping position in preparation for the next cycle.

In accordance with certain further principles of this invention, the reservoir includes a deformable fluid-impermeable bag containing fluid which, when deformed by the application of force thereto, pressurizes the fluid. Cooperating with the deformable reservoir bag is a fluid pressurization means which includes a rigid housing having at least first and second rigid walls between which the bag is located, and an elastically deformable compression member located between at least one of the walls and the bag for applying a force to the bag to pressurize the fluid therein.

In accordance with still further principles of this invention, the chamber in which the fluid charge accumulates, and from which it is pumped, includes a generally cylindrical bore at the opposite ends of which are located the fluid inlet and fluid outlet ports. The valve closure element is slideably positioned within the bore and has a pair of opposite ends which alternately seal the fluid inlet port and fluid outlet port when the valve closure element shifts bidirectionally between its fluid accumulation and fluid pumping positions. The pump element is also bidirectionally shiftable in the bore for movement between a nonpumping position in which it is retracted from the fluid chamber and a pumping position in which it is advanced into the chamber.

As previously noted, when the electromagnetic force generator is actuated, the valve element shifts from its normal position sealing the fluid outlet port to a position sealing the fluid inlet port. Immediately thereafter the pump element advances into the chamber from its normal retracted position to its pumping position, forcibly displacing the accumulated charge from the chamber into the conduit via the fluid outlet port for injection into the body. Upon completion of the pumping action, the electromagnetic force generator is de-energized. When this occurs, the spring returns the valve element to connect the chamber and reservoir via the fluid inlet port while simultaneously sealing the fluid outlet port. The pump element is thereafter returned to its normal retracted position by fluidic forces applied thereto by the pressurized fluid entering the charge accumulation chamber from the reservoir. When the charge accumulation chamber is filled with fluid and the pump element is in its fully retracted position, the apparatus is ready for another charge-injecting cycle.

In accordance with still further principles of this invention designed to promote sterility, the valve and pump assembly includes a flexible, tubular, fluid-impermeable membrane which isolates the charge accumulation chamber from all elements of the system, except the interior of the reservoir and the conduit, thereby effectively hermetically sealing those elements of the system which come into contact with the fluid. In a preferred form, the membrane has a first region surrounding the fluid outlet port of the chamber with respect to which it is in sealed relation, a second region located proximate the fluid inlet port with respect to which it is sealed, and a third region intermediate the first and second regions which is connected to the pump element for movement therewith. As the pump element advances and retracts relative to the charge accumulation chamber, the flexible membrane advances and retracts with it. In this way the fluid charge accumulation chamber and the conduit and reservoir which connect to it, remain isolated from the environment, including the selectively reciprocable pumping element.

These and other advantages, features, and objectives of the invention will become more readily apparent from a detailed description of the preferred embodiment thereof taken in conjunction with the drawings in which:

FIG. 1 is a perspective view of the fluid injection system of this invention.

FIG. 2 is an elevational view in cross-section of the combined pump and valve assembly which facilitates injection into the body of metered quantities of fluid from a reservoir containing pressurized fluid.

FIG. 3 is a cross-sectional view along line 3—3 of FIG. 2.

FIGS. 4, 5, 6, and 7 are vertical cross-sectional views through the combined pump and valve assembly similar to that in FIG. 2, showing the valve closure element and the pump element in the various positions they assume in the process of injecting a charge of fluid into the body.

FIG. 8 is a schematic circuit diagram, in block format, of a control circuit suitable for effecting manual and/or automatic programmed control of the fluid injection system.

With reference to FIG. 1, the fluid injection system of this invention is seen to include a reservoir 10 containing a supply of fluid which is pressurized by fluid pressurization means 12, a combined pump and valve assembly 14 which is in fluid communication with the reservoir 10 for accumulating a charge of fluid of predetermined quantity and pumping the accumulated charge through a suitable injection means 16 into the body, the injection means being in fluid communication with the outlet of the combined pump and valve assembly.

A case or housing 18 encloses the reservoir 10, fluid pressurization means 12, and the major portion of the combined pump and valve assembly 14. The housing 18 also encloses a suitable control circuit for actuating, either manually or automatically in programmed fashion, the combined pump and valve assembly 14 to effect injection of predetermined quantities of fluid on a manual and/or automatically programmed basis. The control circuit includes a manual operator 20 which when manually actuated effects injection of a charge of fluid of predetermined quantity into the body. Also included in the control circuit is a keyboard 21 and associated digital display 22 which facilitates display and entry of data into the control circuit for providing automatic programmed operation of the fluid injection system. Finally, and also forming part of the control circuit housed within the case 18, is a source of electrical power for the control circuit which, in a preferred form, consists of two batteries 23 and 24, one of which serves as a reserve or standby battery.

Alternatively, the control circuit may include two battery compartments, only one of which during normal usage contains a battery, thereby minimizing weight. Both compartments, however, will contain a battery, albeit only briefly, during battery replacement, when the new battery is placed in the previously empty compartment prior to removal of the old battery. In this way, continuity of electrical power can be maintained because the new battery can be installed prior to removing the old battery. Preferably, mechanical interlock means are provided to positively prevent removal of the old battery prior to installation of the new battery, thereby assuring continuity of electrical power.

The fluid reservoir 10, in a preferred form, is a fluid-impermeable flexible bag which is provided with fitting 25 having a fluid exit port 26 which communicates with the interior of the bag. Port 26 is also in fluid communication with the fluid inlet port 28 of the combined pump and valve assembly 14, both of which will be described in more detail hereafter in connection with FIG. 2. The flexible bag 10 is located in a compartment 27 of constant volume formed in the case 18. The compartment 27 is defined by a rear casing wall 30 and an inner dividing wall 32, a bottom wall 34, a top wall 36, and opposite side walls 38 and 40. Wall 32 is provided with an opening 32a through which projects the bag fitting 25 for connection to the combined pump and valve assembly 14. The top wall 36 is connected along its rear edge to the upper edge of the rear wall 30 by a hinge 42 to facilitate access to the interior of the reservoir compartment. Also located in the reservoir compartment is the fluid pressurization means 12 which, in a preferred form, includes a block of elastically compressible foam. In operation, with the flexible bag 10 and the fluid pressurization compressible foam block 12 in the reservoir compartment 10, the top 36 in its closed position, the foam block elastically deforms in compression to apply a force to the adjacent deformable flexible wall of the bag, in turn pressurizing the fluid in the bag. The fluid in reservoir 10 is pressurized to the extent necessary to overcome pressure drops between the reservoir and the fluid charge accumulation chamber of the combined pump and valve assembly 14 to be described in detail hereafter.

If the fluid is liquid, the pressurization means could be pressurized gas within the bag 10, thereby obviating the need for a separate compression means external to the bag.

Alternatively, the fitting 25 could be eliminated and the plastic bag 10 secured directly to the periphery of the right end of the housing 44, discussed in detail hereafter, by heat sealing, that is, by a "plastic weld". In this way the system can be easily hermetically sealed at the time of manufacture. Of course, should this approach be used, the bag preferably should be vacuum filled and the fluid de-aerated prior to filling. Also, since the bag could not be readily refilled by the user, the valve and pump assembly 14 should be designed to be disposable.

The combined pump and valve assembly 14, considered in more detail in conjunction with FIGS. 2 and 3, includes the tubular housing 44 having an internal fluid chamber 46 in the form of a generally cylindrical bore 48 having a longitudinal axis 49. Sealing the right-hand end of the fluid chamber 46 is a plug 50 having a central bore 52 which is coaxial with the bore 48 defining the fluid chamber 46. The bore 52 constitutes the fluid inlet port 28 which establishes a fluid path between the fluid exit port 26 of the reservoir 10 and the fluid chamber 46 of the combined pump and valve assembly 14. The lefthand face of the plug 50 is provided with a circular groove 54 which receives a mating circular flange 56 which is integral with and extends rightwardly from the tubular housing 44. The cooperating flange 56 and groove 54 facilitate a fluid-tight fit between the plug 50 and the tubular housing 44.

The tubular housing 44 includes a flared opening 58 which receives in fluid-sealing relationship the fitting 25 of the reservoir 10 which is provided with a corresponding mating taper on its outer periphery. The fitting 25, which is fabricated of relatively inflexible material, is connected to the flexible bag of the reservoir 10. As previously noted, the fitting 25 also passes through the opening 32a in the divider wall 32 of the case 18.

In addition to the fluid inlet port 28, the housing 44 is also provided with a fluid outlet port 60. The fluid outlet port 60 is defined by the inner end 62a of a rigid tube 62 formed integral with and extending rightwardly from the lefthand end of the tubular housing 44. The tube 62 is coaxial with the fluid inlet port 28 and the longitudinal axis 49 of the bore 48 which defines the fluid chamber 46. The tube 62 terminates at its other end in an outer end 62b which projects leftwardly from and is formed integral with the lefthand end of the tubular housing 44. The outer end 62b of the tube 62 interfits in sealing engagement with a flexible conduit 64 which, in combination with a needle 66, comprises the injection means 16.

The fluid inlet port 28 and the fluid outlet port 60 of the fluid chamber 46 are alternately sealed by a valve closure element 68. The valve closure element 68 is selectively movable in an axial direction parallel to the longitudinal axis 49 of the fluid chamber 46 between a first, or left, position in which the lefthand end 68a seals the fluid outlet port 60, and a second, righthand, position in which the righthand end 68b seals the fluid inlet port 28. A compression coil spring 70 located between the righthand edge of fins 68-1, 68-2, and 68-3 provided on the closure element 68, to be described hereafter, and the righthand surface of the plug 50, biases the valve closure element 68 leftwardly such that it is normally in the position shown in FIG. 2, sealing the fluid outlet port 60 and unsealing the fluid inlet port 28.

The valve closure element 68 includes a generally cylindrical body portion 68d having a diameter less than that of the compression spring 70. Radially extending from the body 68d of the valve closure element 68 at three equally spaced circumferential locations thereabout are the three fins 68-1, 68-2, and 68-3 which are in sliding contact with the inner surface of a cylindrical flexible sealing membrane 71, to be described, which is in intimate contact with the bore wall 48. The circumferential slots 72-1, 72-2, and 72-3 defined by the fins 68-1, 68-2, and 68-3 permit fluid to flow from the fluid inlet port 28, when it is unsealed by reason of the valve closure element 68 being in its left position, into the fluid chamber 46 for subsequent exit through the fluid outlet port 60 when the valve closure element thereafter shifts to its right position and the pump, to be described, is actuated to transfer an accumulated charge of fluid from the fluid chamber 46 through the fluid outlet port 60 into the flexible conduit 64 of the injection means 16. Stated differently, the fins 68-1, 68-2, and 68-3 and the associated slots 72 permit the valve closure element 68 to shift between its left fluid charge accumulating position and its right fluid charge injection position without acting as a piston within the bore 48.

In a preferred form the inner end 62a of the tube 62 which defines the fluid outlet port 60 is shaped in the form of a cone, as is the inner end 52a of the bore 52 which defines the fluid inlet port 28. The conical end 62a of the tube 62 and the conical end 52a of the bore 52 function as conical valve seats. Cooperating with these conical valve seats are conical projections 68a' and 68b' which extend from the opposite ends 68a and 68b, respectively, of the valve closure element 68. When the valve closure element 68 is in its left position, conical projection 68a' seats in conical valve seat 62a which defines the fluid outlet port 60 to seal the fluid outlet port. When the valve closure element 68 is in its rightmost position, conical projection 68b' seats in conical valve seat 52a to seal the fluid inlet port 28. The conical design of the valve closure element ends 68a' and 68b' in combination with the conical valve seats 62a and 52a of the fluid outlet port 60 and fluid inlet port 28 provide a self-centering action for the valve closure element 68 and the associated fluid inlet and fluid outlet port, enhancing the effectiveness of the sealing action.

To facilitate pumped transfer of a charge of fluid accumulated in fluid chamber 46 from the fluid chamber 46 to the conduit 64 via fluid outlet port 60, a pumping element 74 is provided. The pumping element 74, in a preferred form, is an annular ring sized and configuration to surround in sliding relationship the tube 62. The ring 62 normally resides in a nonpumping position as shown in FIG. 2, in which event the volume of chamber 46 is at a predetermined maximum. When actuated by suitable actuating means, to be described, the pump element 74 shifts rightwardly along a path through a pumping stroke into the fluid chamber 46, reducing the volume thereof to a preset lesser value, and thereby forcibly displacing and pumping an accumulated charge of fluid of predetermined amount from the fluid chamber 46 into the conduit 64 of the injection means 16 via the fluid outlet port 60 of the tube 62 for injection into the body.

To seal the fluid chamber 46 with respect to the pump element 74 and housing walls which define the bore 48, a membrane 71 is provided. Membrane 71, which is preferably tubular in form and fabricated of fluid-impermeable flexible material such as latex, includes a first region 71a which snugly embraces and lines the interior of the tube 62, isolating the tube end 62a and pump element 74 from the fluid chamber 46. The flexible membrane region 71a terminates in an outer end 71a' which wraps around the outer end 62b of the tube 62. The membrane 71 includes a second region 71b which lines the major portion of the bore 48, terminating in an outer end 71b' which is sandwiched between the flange 56 and plug groove 54, effectively sealing the walls of the bore 48 from the fluid chamber 46. Intermediate the membrane regions 71a and 71b is located intermediate membrane region 71c which is secured to the outer rightmost annular end 74' of the pump 74 by a suitable adhesive or the like for movement therewith. By virtue of membrane 71, the fluid chamber 46 is isolated from everything, including the pump element 74, except the conduit 64 and the reservoir 10.

As the pump element 74 moves from its nonpumping, leftmost position to its pumping, rightmost position, the volume of the fluid chamber 46 is reduced from a maximum to the extent of entry therein of the pumping element 74. The reduction in volume of the fluid chamber 46, in turn, forcefully displaces and transfers an accumulated charge of fluid from the chamber 46 to the flexible conduit 64 via the fluid outlet port 60. Prior to initiation of the rightward movement of the pump element 74 to effect pumping action from the fluid chamber 46 to the conduit 64, the valve closure element 68 moves from its normal left fluid accumulating position, to its right fluid injecting position, unsealing fluid outlet port 60 and sealing fluid inlet port 28. Shifting of the valve closure element 68 to the right prior to rightward pumping motion of the pump element 74, assures that the accumulated fluid charge in the chamber 46 is transferred to the conduit 64, rather than back into the reservoir, when the pump element 74 shifts rightwardly in a pumping stroke.

Upon completion of the rightward movement of the pump element 74, the valve closure element 68 returns to its leftmost fluid accumulating position under the action of the coil spring 70, sealing fluid outlet port 60 and unsealing fluid inlet port 28. Additionally, the pump element 74 returns to its leftmost position, allowing the fluid chamber 46 to accumulate a charge of fluid from the reservoir 10 prior to the next pumping stroke. Upon movement of the valve closure element from its rightmost position to its leftmost position at the conclusion of a fluid transfer operation, pressurized fluid from the reservoir 10 enters the fluid chamber 46 via the fluid inlet port 28. The presence of pressurized fluid in the fluid chamber 46 is effective to urge the pump element 74 to the left, returning it to its normal, nonpumping position. As noted earlier, throughout the entire pumping stroke, as the pump element 74 moves rightwardly into the fluid chamber 46 and then returns to its leftmost position, the pumping element 74 is isolated from the fluid chamber 46 by the membrane 71.

To effect selective movement of the valve closure element 68 from its left fluid accumulating position to its right fluid injection position prior to a pumping operation and further effect selective movement of the pump element 74 from its left nonpumping position to its rightmost pumping position to effect pumping of an accumulated fluid charge from chamber 46 to conduit 64 via fluid outlet port 60, an actuator 78 is provided, preferably of the electromagnetic force generating variety. The electromagnetic force generator 78, in a preferred form, includes an electrical winding or coil wound around the tubular housing 44 such that it surrounds at least a portion of each of the paths through which the valve element 68 and pump element 74 move during a pumping stroke. In accordance with this form of actuator, the pump element 74 and the valve closure element 68 are permanently magnetically polarized with their left ends functioning as north poles and their right ends functioning as south poles. When the coil 78 is energized, the valve closure element 68 is driven from its normal leftmost fluid accumulation position whereat it is biased by the coil spring 70 to its rightmost fluid injection position. Simultaneously, the pump element 74 is driven from its left nonpumping position to its right pumping position.

If desired, and perhaps essential as a practical matter, the outer wall of the housing 44 and the inner wall of the coil 78 can be provided with complementary mating tapers to assure that the combined valve and pump assembly 14 is inserted into the coil with an orientation appropriate to the polarity of the valve element 68 and the pump element 74.

The magnetic permeability, mass, extent of projection into the coil prior to coil energization for the valve closure element 68 and pump element 74 are selected such that the quotient, Fm/m, where Fm is the element, for the valve closure element 68 exceeds that for the pump element 74. As a consequence, the valve element 68 accelerates more rapidly rightwardly when the coil is energized than does the pump element 74, with the result that at the start of a pumping cycle fluid outlet port 60 is unsealed and fluid inlet port 28 is sealed prior to any substantial rightward pumping motion of the element 74. To enhance the likelihood fluid inlet port 28 is sealed prior to appreciable pumping action occurring, the stroke of the valve element 68 preferably is significantly less than the stroke of pump element 74. The foregoing assures that pumping action of the element 74 transfers the accumulated charge of fluid in chamber 46 to the conduit 64 via fluid outlet port 60 rather than back into the reservoir 10 via fluid inlet port 28.

At the conclusion of the pumping action, that is, when the pump element 74 has reached its rightmost limit of travel, the coil 78 is de-energized. When this occurs, valve element 68 is shifted leftwardly by the coil spring 70 sealing fluid outlet port 60 and unsealing fluid inlet port 28. Leftward movement of valve element 68 also partially returns pump element 74 to its nonpumping position. Pressurized fluid enters the chamber 46 from the reservoir 10 via the fluid inlet port 28. The pressurized fluid acts on the pump element 74, urging it leftwardly to fully return it to its normal leftmost nonpumping position. As the pump element 74 returns to its leftmost position, the volume of the fluid chamber 46 increases to its maximum allowing a charge of fluid to accumulate in the chamber 46 for injection into the body during the next pumping cycle.

The pumping force resulting from the application of electromagnetic forces to the pump element 74 by coil 78 must be sufficient to overcome pressure drops between chamber 46 and the needle 66, as well as injection resistance of body tissue in which the needle is inserted.

With reference to FIGS. 4 through 7, a charge accumulation and pumping sequence will now be described. When the coil 78 is de-energized, the valve closure element 68 and pump element 74 assume the position shown in FIG. 4. The fluid outlet port 60 is sealed and the fluid inlet port 28 is unsealed. Additionally, the pump element 74 is fully retracted, allowing the fluid chamber 46 to be at maximum volume. The valve closure element 68 is held in its leftmost position by the spring 70, and the pump element 74 is held in its left position by the pressurized fluid in chamber 46.

When an injection is desired, the coil 78 is energized, shifting the valve closure element rightwardly such that it seals fluid inlet port 28 and unseals fluid outlet port 60, as shown in FIG. 5. Immediately thereafter the pump element 74 shifts rightwardly, reducing the volume of the chamber 46, transferring the accumulated fluid charge from the chamber 46 via the outlet port 60 to the conduit 64 for injection via the needle 66 into the body as shown in FIG. 6.

Upon the conclusion of the pumping stroke when the pump element 74 has reached its rightmost limit of travel, the coil 78 is de-energized. The spring shifts the closure element 68 leftwardly, sealing fluid outlet port 60 and unsealing fluid inlet port 28, as shown in FIG. 7. Pressurized fluid from the reservoir 10 now enters the chamber 46 via the fluid inlet port 28.

Movement of the valve closure element 68 to the left under the action of the spring 70 upon de-energization of the coil 78, in addition to sealing fluid outlet port 60 and unsealing fluid inlet port 28, is also effective to move the pump element 74 to the left to the position shown in FIG. 7. Thus, upon de-energization of the coil 78 the pump element 74 is partially returned to its normal nonpumping position by the valve closure element 78. Thereafter the pump element 74 is fully returned to its normal nonpumping position, that is, moved from the position shown in FIG. 7 to the position shown in FIG. 4, under the action of the pressurized fluid entering the chamber 46 which exerts a leftwardly force on the pump element 74.

To minimize the possibility the pump element 74 must overcome a back pressure when moving leftwardly, a vent port 77 is provided in the left end of the housing 44 to vent to atmosphere the left portion of the bore 48 in which the pump element 74 reciprocates.

The control circuit shown in FIG. 8 includes, in addition to the electromagnetic force generator 78 which is preferably in the form of an electromagnetic coil, a source of electrical energy 84. In a preferred form, the electrical energy source 84 comprises a pair of batteries 23 and 24 which are connected in electrical parallel circuit relation. Typically, one of the batteries is in energy-supplying relationship to the control circuit, while the other battery functions as a standby or reserve battery. Alternatively, and as noted earlier, to minimize weight during normal usage, the standby battery can be eliminated. However, dual battery compartments are desirable to permit installation of a fresh battery prior to removal of a used battery. If this approach is used, battery interlock means should be provided to prevent removal of the old battery prior to installation of the new one, thereby assuring an uninterrupted supply of battery power.

Also included in the control circuit is a pulse generator 86 which supplies an electrical pulse of requisite duration, voltage, and current to the electromagnetic force-generating coil 78 for energizing it to apply shift forces, indicated by the dotted lines in FIG. 8, to the valve closure element 68 and the pump element 74, moving them to the right as required for a pumping stroke. The pulse generator 86 may take any convenient form and may, for example, include a capacitor which is charged from the power supply 84 for selective discharge through the coil 78. The pulse generator 86 also preferably includes a switch 87 which, when triggered, causes a pulse to be applied, for example, by capacitor discharge, from the pulse generator 86 to the coil 78. The switch 87 is manually triggerable as well as automatically triggerable in accordance with a preselected program. The manual triggering is accomplished with the manual operator 20, while programmable triggering is achieved with a programmable trigger 90 in accordance with a program entered into the system via the keyboard 21. The programmable trigger 90, in the preferred form, includes a specially programmed microcomputer which actuates the switch 87 to effect pulsing of the coil and injection of a pressurized fluid charge into the body in accordance with a schedule entered into the system via the keyboard 21 which is stored in the microcomputer memory.

If desired, the control circuit could include two or more manual operators 20, each of which when actuated provides different doses. For example, one such manual operator, when actuated, could initiate a single dose, that is, a single pulsing of the coil and injection of a single charge, while a second manual operator, when actuated, could initiate a double dose, that is, two sequential pulsings of the coil to provide sequential injection of two charges.

The elements of the system which are in contact with the fluid, such as the reservoir 10, plug 50, valve closure element 68, flexible sealing membrane 71, conduit 64, and needle 66, should be fabricated of a material which is inert and impermeable to the fluid. If the fluid is a solution containing insulin such as used in treating diabetics, or penicillin which is useful in treating persons with pneumonia, a variety of different materials can be utilized, such as, plastics, stainless steel, etc.

In a preferred form of the invention the outside diameter of the tubular housing 44 is 0.283 inches. Assuming a housing diameter as noted, and further assuming that the coil 78 is wound on a "phantom bobbin" so as to minimize air gap losses between the coil and the tubular housing 44, a coil having the following approximate physical and electrical characteristics is suitable:

Number of turns: 5,000
Coil width: 1.71 cm
Number of turns per layer: 136
Number of layers: 37
Total length of wire in winding: 188.7 meters
Total resistance of coil winding: 323 ohms
Required power for application to coil: 3.23 volts at 0.01 amperes
Size and type of wire: No. 37 copper wire with enamel insulation cooperating with a coil of the foregoing description is a pump element having a length of 8.1 mm, a minimum inside diameter of 2.3 mm, and a maximum outside diameter of 5.4 mm; and a valve element having a length of 6.3 mm exclusive of conical projections which are each 1.3 mm in length, and maximum diameters for the finned and unfinned sections of 5.1 mm and 4.0 mm, respectively.

What is claimed is:

1. A fluid injection system comprising:

a fluid reservoir having a fluid exit port, fluid pressurization means for pressurizing fluid in said reservoir to provide pressurized fluid at said reservoir exit port, a conduit insertable in the body having a passage through which fluid passes for injection into the body, a combined valve and pump assembly having (a) an internal fluid charge accumulation chamber of predetermined constant maximum volume provided with a fluid inlet port in fluid communication with said reservoir exit port and a fluid outlet port in fluid communication with said conduit passage, (b) a valve closure element located within said chamber and movable between a charge accumulation position in which said closure element seals said fluid outlet port and unseals said fluid inlet port to facilitate admission of pressurized fluid into said chamber to accumulate said charge, and a charge injection position in which said closure element seals said inlet port and unseals said outlet port to permit said accumulated charge to be pumped from said chamber to said conduit for injection.

(c) a pump element located for movement through a pumping stroke of preset length within said chamber between a nonpumping position in which the volume of said chamber is at said maximum to facilitate accumulation of a fluid charge of preset volume in said chamber when said closure element is in said charge accumulation position, and a pumping position in which the volume of said chamber is reduced to less than said maximum to transfer said accumulated fluid charge of preset volume from said chamber into said conduit when said closure element is in said charge injection position, and (d) actuating means for selectively alternatively placing said closure element and said pump element (1) in said charge accumulation and nonpumping positions, respectively, to facilitate transfer of a fluid charge from said pressurized reservoir to said chamber, or (2) in said charge injection and pumping positions, respectively, to facilitate pumped transfer of said accumulated fluid charge from said chamber to said conduit for injection into said body.

2. The system of claim 1 wherein said actuating means includes a spring to bias said valve closure element toward said charge accumulation position.

3. The system of claim 1 wherein said valve closure element and said pump element are permanently magnetically polarized and wherein said actuating means include electromagnetic force generating means acting on said valve closure element and said pump element to facilitate charge accumulation in said chamber and pumped transfer of said accumulated charge from said chamber to said conduit for injection into said body.

4. The system of claim 1 wherein said chamber includes a bore defined by interior walls and having a longitudinal axis, said closure element moves bidirectionally in a first path along said axis in said bore between said charge accumulation and charge injection positions, and said pumping element moves bidirectionally along said axis in a second path in said bore between said pumping and nonpumping positions.

5. The system of claim 4 wherein said fluid inlet and fluid outlet ports are located at opposite ends of said first path, and wherein said valve closure element has a pair of opposite ends for alternately sealing said fluid outlet and fluid inlet ports when said valve closure element is shifted along said first path between its charge accumulation and charge injection positions.

6. The system of claim 5 wherein said combined valve and pump assembly further includes a tube disposed in said chamber generally parallel to said longitudinal axis along said second path, said tube having an inner end defining said fluid outlet port and an outer end connecting to said conduit, and wherein said pump element surrounds said tube and is bidirectionally shiftable therealong over said second path between said pumping and nonpumping positions.

7. The system of claim 6 wherein said valve closure element and said pump element are permanently magnetically polarized and wherein said actuating means includes electromagnetic force generating means acting on said valve closure element and said pump element to facilitate charge accumulation in said chamber and pumped transfer of said accumulated charge from said chamber to said conduit for injection into said body.

8. The system of claim 6 wherein said opposite ends of said valve closure element each have conical projections thereon, and wherein said fluid inlet and fluid outlet ports each include conical valve seats against which said respectively associated conical projections of said valve closure element seat for alternately sealing said fluid outlet and fluid inlet ports when said valve closure element shifts between its charge accumulation and charge injection positions.

9. The system of claim 6 wherein said combined valve and pump assembly further include a flexible tubular fluid-impermeable membrane having (a) a first region surrounding said inner end of said tube and being fixed relative thereto, (b) a second region located proximate said interior wall of said bore, and (c) a third region intermediate said first and second regions which is connected to said pump element for movement therewith, said flexible membrane isolating said pump element from fluid in said chamber throughout movement of said pump element through said pumping stroke along said second path.

10. The system of claim 9 wherein said first region of said membrane also extends along the interior of said tube to said outer end thereof, said first region of said tubular membrane terminating in an opening which is sealed relative to said outer end of said tube.

11. The system of claim 10 wherein said bore includes a section surrounding said inlet port and wherein said second region of said tubular membrane terminates in an opening which is sealed relative to said section of said bore.

12. The system of claim 7 wherein said electromagnetic means includes an electrical coil surrounding said bore establishing a magnetic flux path along said axis, said coil surrounding at least a portion of said first and second paths of said valve element and pumping element, respectively.

13. The system of claim 3 wherein said actuating means includes an electrical pulse generator for intermittenly energizing said electromagnetic means to intermittently generate said electromagnetic forces and thereby intermittently facilitate charge accumulation in said chamber and pumped transfer of said accumulated charge from said chamber to said conduit for injection into said body.

14. The system of claim 1 wherein said valve closure element and said pump element are permanently magnetically polarized and wherein said actuating means includes a spring to bias said valve closure element toward said charge accumulation position, and wherein said actuating means further includes an intermittently energized electromagnetic force generating means acting on said valve closure element and said pump element to intermittently move said valve closure element and said pump element to said charge injection and pumping positions, respectively, to facilitate pumped transfer of said accumulated charge from said chamber to said conduit for injection into said body, said valve closure element being moved by said spring to said charge accumulation position to admit pressurized fluid from said reservoir into said chamber to accumulate said charge when said electromagnetic means is de-energized, said admitted pressurized fluid in said chamber in turn moving said pump element to said nonpumping position.

15. The system of claim 1 wherein said fluid reservoir includes a flexible wall which moves inwardly when a force is applied thereto to pressurize said fluid, and wherein said fluid pressurization means includes an elastically deformable member which when elastically deformed applies to a force to said flexible wall to pressurize said fluid in said reservoir.

16. The system of claim 1 wherein said fluid reservoir includes a deformable fluid-impermeable bag containing fluid which when deformed by the application of force thereto pressurizes said fluid therein, and wherein said fluid pressurization means includes a rigid housing for said bag having at least first and second walls between which said bag is located, and an elastically deformable compression member located between at least one of said walls and said bag for applying a force to said bag to pressurize said fluid in said bag.

17. The system of claim 13 wherein said actuating means further includes a battery power supply connected to said pulse generator, and selectively triggerable switch means connected in circuit with said pulse generator which when triggered, is effective to cause said pulse generator to energize said electromagnetic means.

18. The system of claim 17 wherein said actuating means further includes a manually operable means for triggering said switch means as desired to effect an injection on demand.

19. The system of claim 17 wherein said actuating means further includes a programmable means for automatically triggering said switch means in conformity with a pre-selected program of desired time-spaced injections for effecting injections automatically on a programmed basis.

20. The system of claim 17 wherein said actuating means includes a manually operable means for triggering said switch means as desired to effect an injection on demand, and a programmable means for automatically triggering said switch means in conformity with a pre-selected program of desired time-spaced injections for effecting injections automatically on a programmed basis.

21. The system of claim 4 wherein said combined valve and pump assembly includes a flexible tubular fluid-impermeable membrane having (a) a first region surrounding said fluid outlet and fixed relative thereto, (b) a second region located proximate said interior wall of said base, and (c) a third region intermediate said first and second regions which is connected to said pump element for movement therewith, said flexible membrane isolating said pump element from fluid in said chamber throughout movement of said pump element through said pumping stroke along said second path.

22. The system of claim 21 wherein said bore includes a section surrounding said inlet port and wherein said second region of said tubular membrane terminates in an opening which is sealed relative to said section of said bore.

23. The system of claim 5 wherein said valve closure element and said pump element are permanently magnetically polarized and wherein said actuating means includes a spring to bias said valve closure element toward said charge accumulation position, and wherein said actuating means further includes an intermittently energized electromagnetic force-generating coil surrounding said bore and at least portions of said first and second paths for acting on said valve closure element and said pump element to intermittently move said valve closure element and said pump element to said charge injection and pumping positions, respectively, to facilitate pumped transfer of said accumulated charge from said chamber to said conduit for injection into said body, said valve closure element being moved by said spring to said charge accumulation position to admit pressurized fluid from said reservoir into said chamber to accumulate said charge when said electromagnetic means is de-energized, said admitted pressurized fluid in said chamber in turn, moving said pump element to said nonpumping position.

24. The system of claim 23 wherein said valve closure element and said pump element are constructed relative to each other to provide said valve closure element with greater acceleration than said pump element when both are simultaneously subjected to magnetic forces from said electromagnetic force-generating coil to facilitate movement of said valve closure element to said charge injection position before appreciable movement of said pump element occurs from said nonpumping position toward said pumping position.

25. The system of claim 24 wherein the distance between said charge accumulation and charge injection positions is less than the length of said pumping stroke, to further enhance movement of said valve closure element to said charge injection position before appreciable movement of said pump element occurs from said nonpumping position toward said pumping position.

26. The system of claim 16 wherein the bag is heat sealed to the combined valve and pump assembly to provide a hermetic seal therebetween.

27. The system of claim 1 wherein said fluid is a liquid and said means to pressurize said fluid reservoir includes pressurized gas within said reservoir.

* * * * *